(12) United States Patent
Graham et al.

(10) Patent No.: US 8,858,961 B2
(45) Date of Patent: Oct. 14, 2014

(54) COMPOSITIONS CONTAINING ALPHA-2-ADRENERGIC AGONIST COMPONENTS

(75) Inventors: Richard S. Graham, Irvine, CA (US); Peter G. Bakhit, Huntington Beach, CA (US); Orest Olejnik, Coto De Caza, CA (US)

(73) Assignee: Allergan, Inc., Irvine, CA (US)

( * ) Notice: Subject to any disclaimer, the term of this patent is extended or adjusted under 35 U.S.C. 154(b) by 784 days.

(21) Appl. No.: 12/482,783

(22) Filed: Jun. 11, 2009

(65) Prior Publication Data

US 2009/0312337 A1   Dec. 17, 2009

Related U.S. Application Data

(63) Continuation-in-part of application No. 10/928,906, filed on Aug. 27, 2004, now abandoned, which is a continuation-in-part of application No. 10/691,912, filed on Oct. 22, 2003, now abandoned, which is a continuation of application No. 10/236,566, filed on Sep. 6, 2002, now Pat. No. 6,641,834, which is a continuation of application No. 09/904,018, filed on Jul. 10, 2001, now Pat. No. 6,627,210.

(60) Provisional application No. 60/218,200, filed on Jul. 14, 2000.

(51) Int. Cl.
| | |
|---|---|
| A61K 9/00 | (2006.01) |
| A61K 31/715 | (2006.01) |
| A61K 31/498 | (2006.01) |
| A61K 31/734 | (2006.01) |
| A61K 31/716 | (2006.01) |
| A61K 47/32 | (2006.01) |
| A61K 31/78 | (2006.01) |
| A61K 47/38 | (2006.01) |

(52) U.S. Cl.
CPC ............. *A61K 9/0048* (2013.01); *A61K 31/715* (2013.01); *A61K 31/498* (2013.01); *A61K 31/734* (2013.01); *A61K 31/716* (2013.01); *A61K 47/32* (2013.01); *A61K 31/78* (2013.01); *A61K 47/38* (2013.01)
USPC .......................................................... 424/400

(58) Field of Classification Search
USPC ......................................................... 424/400
See application file for complete search history.

(56) References Cited

U.S. PATENT DOCUMENTS

| | | | |
|---|---|---|---|
| 3,278,447 | A | 10/1966 | McNicholas |
| 3,300,511 | A | 1/1967 | Stahle et al. |

(Continued)

FOREIGN PATENT DOCUMENTS

| | | |
|---|---|---|
| CA | 2048315 | 1/1992 |
| EP | 0426390 | 5/1991 |

(Continued)

OTHER PUBLICATIONS

Schuman (Surv of Ophthalmology, vol. 41, Supp 1 (1996) S27-S37).*

(Continued)

*Primary Examiner* — Benjamin Packard
(74) *Attorney, Agent, or Firm* — Lorenz Siddiqi

(57) ABSTRACT

Compositions useful for improving effectiveness of alpha-2-adrenergic agonist components include carrier components, alpha-2-adrenergic agonist components, solubility enhancing components which aid in solubilizing the alpha-2-adrenergic agonist components. In one embodiment, the alpha-2-adrenergic agonist components include alpha-2-adrenergic agonists. In another embodiment, the solubility enhancing components include carboxymethylcellulose.

9 Claims, 1 Drawing Sheet

(56) References Cited

U.S. PATENT DOCUMENTS

| | | |
|---|---|---|
| 3,890,319 A | 6/1975 | Danielewicz et al. |
| 4,407,791 A | 10/1983 | Stark |
| 4,499,077 A | 2/1985 | Stockel et al. |
| 4,530,920 A | 7/1985 | Nestor et al. |
| 4,806,556 A | 2/1989 | Portoghese |
| 5,021,416 A | 6/1991 | Gluchowski |
| 5,091,528 A | 2/1992 | Gluchowski |
| 5,202,128 A | 4/1993 | Morella et al. |
| 5,215,991 A | 6/1993 | Burke |
| 5,352,796 A | 10/1994 | Hoeger et al. |
| 5,424,078 A | 6/1995 | Dziabo et al. |
| 5,459,133 A | 10/1995 | Neufeld |
| 5,597,559 A * | 1/1997 | Olejnik et al. ............. 424/78.04 |
| 5,703,077 A | 12/1997 | Burke et al. |
| 5,719,197 A | 2/1998 | Kanios et al. |
| 5,725,887 A | 3/1998 | Martin et al. |
| 5,776,445 A | 7/1998 | Cohen et al. |
| 5,814,638 A | 9/1998 | Lee et al. |
| 5,834,470 A | 11/1998 | Mauer |
| 5,834,502 A | 11/1998 | Cheng et al. |
| 5,994,110 A | 11/1999 | Mosbach et al. |
| 6,066,675 A * | 5/2000 | Wen et al. ..................... 514/649 |
| 6,166,012 A * | 12/2000 | Muller et al. ............. 514/235.5 |
| 6,316,441 B1 | 11/2001 | Dean et al. |
| 6,358,935 B1 | 3/2002 | Beck |
| 6,562,873 B2 | 5/2003 | Olejnik et al. |
| 6,641,834 B2 | 11/2003 | Olejnik |
| 6,673,337 B2 | 1/2004 | Olejnik et al. |
| 2002/0010202 A1 | 1/2002 | Garst |
| 2002/0032201 A1 | 3/2002 | Olejnik et al. |
| 2003/0045524 A1 | 3/2003 | Woodward et al. |

FOREIGN PATENT DOCUMENTS

| | | |
|---|---|---|
| EP | 0550921 | 7/1993 |
| EP | 0609961 | 8/1994 |
| WO | 94/16685 | 8/1994 |
| WO | 98/47878 | 10/1998 |
| WO | 99/43299 | 9/1999 |
| WO | 99/51273 | 10/1999 |
| WO | 0012137 | 3/2000 |
| WO | 0019981 | 4/2000 |
| WO | 0049990 | 8/2000 |
| WO | 2004/082625 | 9/2004 |
| WO | 2004/087098 | 10/2004 |

OTHER PUBLICATIONS

US 5,776,447, 07/1998, Cohen et al. (withdrawn).
Paragraph IV Certification by Alcon Research, Ltd.-Dated Jul. 6, 2004.
Abstract-XP-002190601-JP 05271053, Oct. 19, 1993.
K. Parfitt (ED): *Martindale, the complete drug reference*, 1999, Thirty-second edition, p. 834, left-hand column, "Brimonidine Tartrate", lines 24-52.
A. Osol (ED): *Remington's Pharmaceutical Sciences*, 1980, 16$^{th}$ Edition, Chapter 86: D. Deardoff, Ph.D., "Ophthalmic preparations", p. 1498-1517.
Remington's Pharmaceutical Sciences, Eighteenth Edition, 1990, pp. 1304-1305.
L. Katz: "Twelve-Month Evaluation of Brimonidine-Purite Versus Brimonidine in Patients With Glaucoma or Ocular Hypertension", Glaucoma 2002, 11(2); 119-126.

* cited by examiner

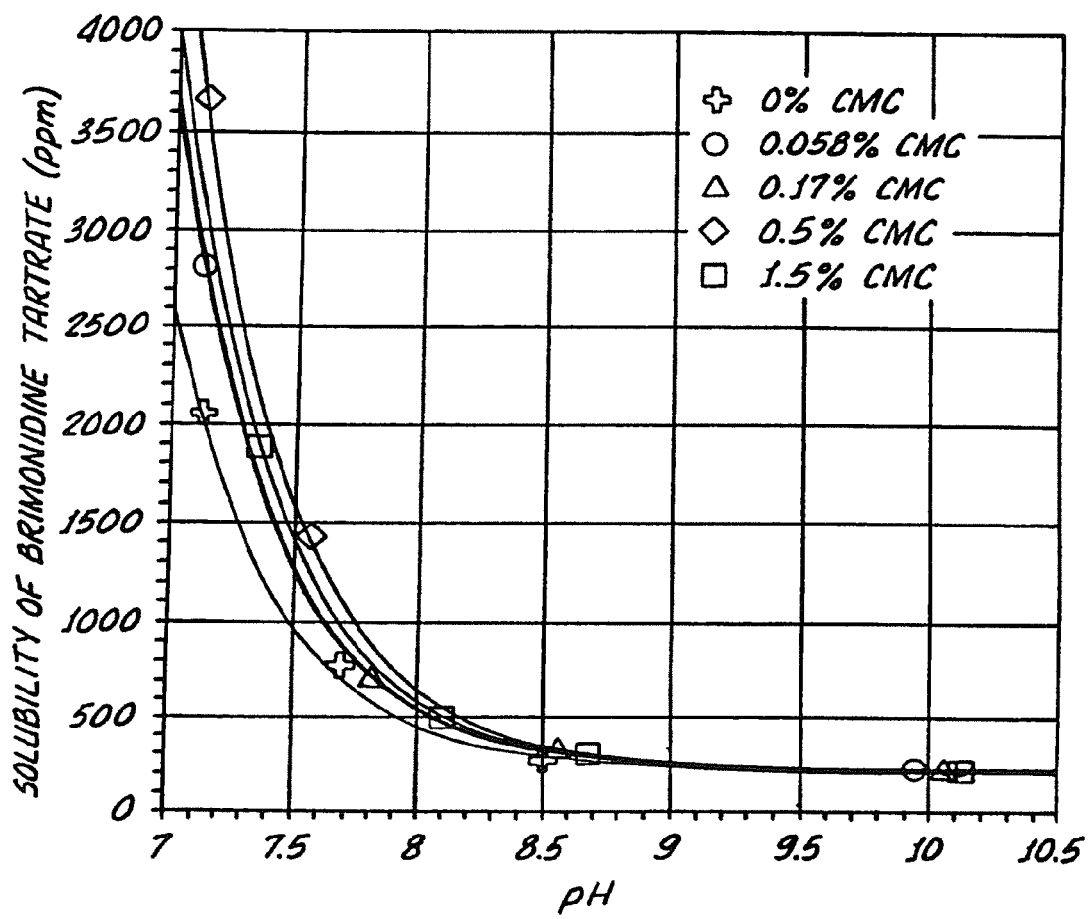

COMPOSITIONS CONTAINING ALPHA-2-ADRENERGIC AGONIST COMPONENTS

This application is a continuation-in-part of U.S. patent application Ser. No. 10/928,906 filed Aug. 27, 2004 which is a continuation-in-part of U.S. patent application Ser. No. 10/691,912, filed Oct. 22, 2003 which is a CON of 10/236,566 filed Sep. 6, 2002, now U.S. Pat. No. 6,641,834; which is CON of 09/904,018 filed Jul. 10, 2001, now U.S. Pat. No. 6,627,210; which claims benefit of 60/218,200 filed Jul. 14, 2000, all of which are hereby incorporated reference herein.

BACKGROUND OF THE INVENTION

The present invention relates to compositions containing alpha-2-adrenergic agonist components. More particularly, the invention relates to such compositions in which the alpha-2-adrenergic agonist components have enhanced solubility at the therapeutically effective concentrations, in which a solution comprising the alpha adrenergic components have substantially similar efficacy at a given pH and concentration as compared to a second solution comprising the alpha adrenergic component at a more acid pH and higher concentration.

Alpha-2-adrenergic agonist components include chemical entities, such as compounds, ions, complexes and the like, which are effective to act on or bind to alpha-2-adrenergic receptors and provide a therapeutic effect. As used herein, the term the term "alpha-2-adrenergic agonist component" means the agonists themselves and any and all precursors, salts and esters thereof, metabolites thereof and combinations thereof.

One of the continuing challenges of formulating compositions having alpha-2-adrenergic agonist components is to render such components more effective. For example, alpha-2-adrenergic agonist components in liquid compositions often benefit from being soluble in the liquid carriers of such compositions. Such solubility promotes uniform and accurate administration.

Additionally, the dispensed or administered alpha-2-adrenergic agonist components should advantageously be soluble in biological systems or environments, for example, for effective or enhanced in vivo diffusion through cell membranes or lipid bilayers. Some alpha-2-adrenergic agonist components, with higher pKa's, greater than about 7, including, for example, brimonidine, tend to diffuse very well through lipid membranes at pH values near or above their pKa, because when in a solution in such circumstances they are predominantly uncharged in neutral to alkaline biological environments. Being more hydrophobic, at this raised pH they are better able to penetrate cellular membranes.

However, at pH values above about 7 a countervailing factor comes into play. Some of these same alpha-2-adrenergic agonist components tend to become less soluble at neutral to alkaline biological pH values in aqueous solutions. Such a decrease in aqueous solubility means that less of the active agent is available in solution to penetrate cellular membranes in order to deliver its therapeutic effect. Thus, even though the soluble compound is more able to penetrate cellular membranes because of its uncharged state, there is less of the component present in solution to provide such a therapeutic effect. Thus, there is a risk that precipitation of the alpha-2-adrenergic agonist component at pH values above about 7.0 will render the alpha-2-adrenergic agonist components less effective and/or their therapeutic effects more variable at a given dosage.

Furthermore, solubilized alpha-2-adrenergic agonist components provide other benefits, for example, reduced irritation to tissues that interact with alpha-2-adrenergic agonist components, than do insoluble alpha-2-adrenergic agonist components.

A specific alpha-2-adrenergic agonist, brimonidine, has been sold as a 0.2% aqueous ophthalmic solution under the trade name ALPHAGAN®. This solution comprises 0.2% brimonidine tartrate, and is formulated at pH 6.5 in a citrate buffer with 0.05% benzalkonium chloride as a preservative.

Additionally, brimonidine is also marketed as a 0.15% ophthalmic solution under the trade name ALPHAGAN P®. This solution is formulated at pH 7.2 and contains carboxymethylcellulose and 0.005% of a stabilized oxy-chloro preservative (PURITE®).

Katz, et al., *J. Glaucoma* 11:119 (April 2002), entitled *Twelve-Month Evaluation of Brimonidine Purite Versus Brimonidine in Patients with Glaucoma or Ocular Hypertension* discloses that a formulation containing 0.15% brimonidine and a PURITE® preservative has a similar efficacy when administered topically in lowering intraocular pressure as a second formulation containing 0.2% brimonidine. This paper is hereby incorporated by reference as part of this disclosure.

There continues to be a need for new compositions containing alpha-2-adrenergic agonist components which combine a high degree of efficacy with a low incidence of side effects, including systemic side effects.

SUMMARY OF THE INVENTION

The present invention is based on the discovery of new alpha-2-adrenergic agonist component-containing compositions which are able to deliver the active agent more effectively to the target cell or tissue. This increase in efficacy can be attributed to two factors: solubility and a neutral or alkaline pH. It will be understood that pH values given in this specification are to be measured at room temperature.

In one embodiment, the present compositions contain certain materials which are effective in at least aiding or assisting in solubilizing the alpha-2-adrenergic agonist components in the compositions, and preferably in environments to which the compositions are administered or introduced, for example, biological environments, such as the human eye. Preferably, aqueous solubility of alpha-2-adrenergic agonist components in accordance with the present invention facilitates predicable and consistent delivery of the therapeutic effect to the target cell or tissue.

In another embodiment, the present invention is drawn to aqueous solutions containing alpha-2-adrenergic agonist components which have a pH above about 7.0, preferably between about pH 7.0 and about pH 8.5, more preferably between about pH 7.2 and about pH 8.2 or about pH 7.2, even more preferably between about pH 7.5 and about pH 8.0 or at about pH 7.7. In this embodiment the aqueous solution may optionally contain a material or mixture of materials which is effective in at least aiding or assisting in solubilizing the alpha-2-adrenergic agonist components. Alternatively, the solution may lack such exogenous solubilizing materials and comprise or consist essentially of a soluble alpha-2-adrenergic agonist component in aqueous solution at a pH value as indicated above. In this aspect, the neutral or alkaline pH permits the passage of the alpha-2-agonist component through cellular membranes more easily.

Thus, when the pH of the soluble alpha-2-adrenergic agonist component is above about 7.0, it aids in the transport of such components across lipid membranes. Also, since the alpha adrenergic components are soluble, the dosage of the alpha-2-adrenergic agonist is reliable and reproducible.

Certain alpha-2-adrenergic components have been known to have undesirable side effects. For example, clonidine and tizanidine have been shown to have respiratory and cardiovascular depressive and sedative effects when administered systemically. Thus, any alpha-2-adrenergic agonist formulation in which efficacy can be maintained at a lower effective dose than is commonly used would be clearly advantageous.

In another aspect of the invention, alpha-2-adrenergic agonist component-containing compositions have been discovered which include preservatives that provide substantial advantages, for example, reduced adverse interactions with the alpha-2-adrenergic agonist components and/or with the patients to whom the compositions are administered, while maintaining preservative effectiveness. Preferably, the alpha adrenergic composition is brimonidine.

The present compositions preferably enhance or maintain the effectiveness of previous alpha-2-adrenergic agonist components, while providing additional benefits not present in prior formulations. This is accomplished by keeping the alpha-2-adrenergic agonist component in aqueous solution while simultaneously maintaining a pH value above about 7.0, preferably between about pH 7.0 and about pH 8.5, more preferably between about pH 7.2 and about pH 8.2 or about pH 7.2, even more preferably between about pH 7.5 and about pH 8.0 or at about pH 7.7. By increasing the membrane permeability of the alpha-2-adrenergic agonist component it is possible to lower the concentration of the alpha 2 agonist in the administered formulation, particularly (but not exclusively) brimonidine, thereby reducing any systemic side effects, particularly when the formulation is given systemically.

Within the ambit of some embodiments of the present invention the concentration of brimonidine (including and its pharmaceutically acceptable salts such as the tartrate) in a topical ophthalmic formulation may be reduced below 0.2% (w/v) (preferably between about 0.01% and about 0.1% (w/v)) while maintaining the same or substantially similar efficacy as the product ALPHAGAN®; a 0.2% brimonidine tartrate formulation having a pH of about pH 6.6 to about pH 6.8. In another embodiment, the concentration of brimonidine is preferably about 0.01% to about 0.15% (w/v) at a pH above about 7.0 (preferably about pH 7.2-, about pH 7.7, with any difference in efficacy between the two formulations lacking any substantial difference in efficacy.

As shown in FIG. 1, the solubility of a representative alpha-2-adrenergic agonist, 5-bromo-6-(2-imidozolin-2-ylamino) quinoxaline tartrate, decreases as the pH of the aqueous solution increases. The pKa of 5-bromo-6-(2-imidozolin-2-ylamino) quinoxaline is about 7.4. As the solution becomes more alkaline, the majority of molecules in solution become electronically neutral, and therefore increasingly hydrophobic.

FIG. 1 shows that various solutions containing 5-bromo-6-(2-imidozolin-2-ylamino) quinoxaline all share the same general trend; their solubility decreases with increasing pH. The curve identified with a cross (*) is an aqueous solution containing the active agent with no added carboxymethylcellulose (CMC); such solutions are within the scope of certain embodiments of this invention.

In one aspect, the effectiveness of the alpha-2-adrenergic agonist components are increased by increasing the solubility of the alpha-2-adrenergic agonist components, preferably at pH values higher than neutral. In this aspect of the invention, the invention includes, in addition to the alpha-2-adrenergic agonist components, solubility enhancing components (SECs) in amounts effective to enhance the solubility of the alpha-2-adrenergic agonist components at a given pH. Preferably, these SECs are anionic in nature, and even more preferably, they are polymeric in nature. In one embodiment the SEC is a cellulose derivative, in another embodiment the SEC is not a cellulose derivative or a cyclodextrin.

In this aspect of the invention, the alpha-2-adrenergic agonist components are more soluble in the present compositions having, for example, pH values of about 7 or greater, relative to substantially identical compositions which lack the SECs. In another embodiment, the alpha-2-adrenergic agonist components of the present compositions are more soluble in neutral or alkaline biological environments into which the compositions are administered relative to alpha-2-adrenergic agonist components in similar compositions without the SECs. This latter aspect is particularly true when the alpha-2-adrenergic agonist components are delivered to their site of action topically.

The alpha-2-adrenergic agonist components used in the present invention include imino-imidazolines, imidazolines, imidazoles, azepines, thiazines, oxazolines, guanidines, catecholamines, biologically compatible salts and esters and mixtures thereof. Preferably, the alpha-2-adrenergic agonist components include quinoxaline components. Quinoxaline components include quinoxaline, biologically compatible salts thereof, esters thereof, other derivatives thereof and the like, and mixtures thereof. Non-limiting examples of quinoxaline derivatives include (2-imidozolin-2-ylamino) quinoxaline, 5-bromo-6-(2-imidozolin-2-ylamino) quinoxaline, and biologically compatible salts thereof and esters thereof, preferably the tartrate of 5-bromo-6-(2-imidozolin-2-ylamino) quinoxaline, and the like and mixtures thereof. Hereinafter, the tartrate of 5-bromo-6-(2-imidozolin-2-ylamino) quinoxaline is referred to as "brimonidine tartrate."

In a preferred embodiment, the alpha-2-adrenergic agonist components, such as those listed above, are selective for the alpha-2A-adrenergic receptors, alpha-2B-adrenergic receptors and/or alpha-2D-adrenergic receptors in relation to their activity at one or more other adrenergic receptor. Preferably, the alpha-2-adrenergic agonist components are selective for the alpha-2A-adrenergic receptors, alpha-2B-adrenergic receptors and/or alpha-2D-adrenergic receptors in comparison to their activity at the alpha-1-adrenergic receptors.

In one embodiment, the alpha-2-adrenergic agonist components are at least about 30% uncharged in the presently disclosed and claimed compositions, preferably at least about 50% uncharged. Those of skill in the art will appreciate that the pKa is the negative log of the ionization constant (or the pH at which the compound is 50% ionized), and that a reference in this application to a specific percent of the compound uncharged (such as, for example, at least 30% or 50% uncharged) is intended to refer to the compound on a stoichiometric basis.

Even more preferably, the soluble alpha-2-adrenergic agonist components are also at least about 30% uncharged, or at least about 50% uncharged in the biological environment into which the compositions are administered.

When the alpha-2-adrenergic agonist components are formulated with an SEC, the SEC may include a non-ionic or polyanionic component. As used herein, the term "polyanionic component" refers to a chemical entity, for example, an ionically charged species, such as an ionically charged polymeric material, which includes multiple discrete anionic charges. Non-ionic SECs may include polyvinyl alcohol (PVA), polyvinyl pyrrolidone (povidone), and various gums and other non-ionic agents.

In a preferred embodiment, the SEC is a polyanionic component, which may be selected from polymeric materials having multiple anionic charges, and mixtures thereof.

Particularly useful polyanionic components are selected from anionic polymers derived from acrylic acid (meaning to include polymers from acrylic acid, acrylates and the like and mixtures thereof), anionic polymers derived from methacrylic acid (meaning to include polymers from methacrylic acid, methacrylates, and the like and mixtures thereof), anionic polymers derived from alginic acid (meaning to include alginic acid, alginates, and the like and mixtures thereof), anionic polymers of amino acids (meaning to include polymers of amino acids, amino acid salts, and the like and mixtures thereof), and the like, and mixtures thereof. Very useful polyanionic components are those selected from anionic cellulose derivatives and mixtures thereof, especially carboxymethyl cellulose and its derivatives.

The polyanionic component preferably is sufficiently anionic to interact with or otherwise affect or increase the solubility of, the alpha-2-adrenergic components. This interaction preferably is sufficient to render the alpha-2-adrenergic components substantially completely soluble at therapeutically effective concentrations. The amount of SEC in the composition preferably is in the range of about 0.1% (w/v) to about 30% (w/v), more preferably about 0.2% (w/v) to about 10% (w/v), and even more preferably about 0.2% (w/v) to about 0.6% (w/v).

The compositions may also include carrier components, for example, aqueous liquid carrier components. In one embodiment, the compositions have pH values of above about 7.0, preferably between about pH 7.0 and about pH 8.5, more preferably between about 7.2 and about 8.2, even more preferably between about 7.5 and about 8.0. Furthermore, preferably these compositions are ophthalmically acceptable.

In another preferred embodiment, a composition is provided which includes an alpha-2-adrenergic agonist component in an amount effective to provide at least one therapeutic benefit to a patient to whom the composition is administered, an anionic cellulose derivative in an amount effective to increase the solubility of the alpha-2-adrenergic agonist component and an aqueous liquid carrier component. The alpha-2-adrenergic agonist component preferably comprises a tartrate of 5-bromo-6-(2-imidozolin-2-ylamino) quinoxaline. The anionic cellulose derivative preferably comprises a carboxymethylcellulose. The concentration of the anionic cellulose derivative in the composition should be about 0.2% (w/v) to about 0.6% (w/v).

In the preferred embodiments of the composition of the invention, the composition contains 5-bromo-6-(2-imidozolin-2-ylamino) quinoxaline or a salt or ester thereof; the concentration of this alpha-2-adrenergic agonist is less than 0.2%; preferably between 0.2% (w/v) and about 0.001% (w/v), more preferably about 0.15% (w/v) or less, even more preferably between 0.15% (w/v) and about 0.001% (w/v), most preferably about 0.1% (w/v) or less.

Also, the preferred embodiments of the composition of this invention comprise an aqueous solution at neutral or alkaline pH. Preferably the composition is about pH 7.0 or greater at room temperature or about 7.2 or greater at room temperature, even more preferably about 7.5 or greater at room temperature, most preferably at about 7.7 or greater at room temperature.

In a preferred embodiment, the present compositions are ophthalmically acceptable, e.g. the compositions do not have deleterious or toxic properties which could substantially harm the eye of the human or animal to whom the compositions are administered.

In one aspect of the invention, complexes may be formed in the compositions. In one embodiment, the complexes include monomer units derived from at least one quinoxaline component. In a preferred embodiment, the complexes of the present invention are dimers. In a particularly preferred embodiment, the complexes are complexes, especially dimers, of brimonidine tartrate.

In another broad aspect of the present invention, compositions are provided which comprise an alpha-2-adrenergic agonist component and a preservative component in an effective amount to at least aid in preserving the compositions. Preferably, the preservative components include oxy-chloro components, such as compounds, ions, complexes and the like which are biologically acceptable, chemically stable and do not substantially or significantly detrimentally affect the alpha-2-adrenergic agonist component in the compositions or the patients to whom the compositions are administered. Such compositions preferably are substantially free of cyclodextrins in the compositions or the patients to whom the compositions are administered.

Any feature or combination of features described herein are included within the scope of the present invention provided that the features included in any such combination are not mutually inconsistent as will be apparent from the context, this specification, and the knowledge of one of ordinary skill in the art. Whenever numerical ranges are indicated herein, they should be understood as disclosing each and every individual value that fall within the range, i.e. that they are a mere abbreviation of listing all these values.

Additional advantages and aspects of the present invention are apparent in the following detailed description and claims.

BRIEF DESCRIPTION OF THE DRAWING

FIG. 1 is a graph of soluble brimonidine tartrate in aqueous solution at room temperature plotted versus pH at various carboxymethylcellulose concentrations.

DETAILED DESCRIPTION OF THE INVENTION

Therapeutically effective compositions comprising alpha-2-adrenergic agonist components are provided. These compositions provide the advantage of being formulated at neutral or alkaline pH, thus providing a dosage of the active agent in a substantially uncharged, more lipid soluble form. Since the alpha-2-adrenergic agonist components are more able to cross cellular membranes the compositions of the present invention maintain or increase efficacy relative to a composition formulated at acid pH.

Each aspect of the compositions of the invention is necessarily therapeutically effective; a composition which is not therapeutically effective is not intended to fall within the ambit of any claim hereof. By "therapeutically effective" is meant that the composition is able to exert a statistically significant medically beneficial effect when used as prescribed or directed, as compared to a placebo. Thus, a composition prescribed for use to lower intraocular pressure is and shall be intended to refer to a composition having a statistically significant ocular hypotensive effect when used as directed.

In one embodiment, the present invention envisages a composition, such as a topical ophthalmic composition, comprising an alpha-2-adrenergic agonist component formulated in aqueous solution at a pH such that the alpha adrenergic component is at least 30%, at least 40%, at least 50% or at least 60% uncharged.

In a particularly preferred embodiment, the invention is directed to a composition comprising 5-bromo-6-(2-imidozolin-2-ylamino) quinoxaline, or salts thereof, wherein the solution is formulated at a concentration of less than 0.2% (w/v). Preferably the active ingredient is present in the composition at a concentration of preferably between 0.2% (w/v) and about 0.001% (w/v), more preferably about 0.15% (w/v) or less, even more preferably between 0.15% (w/v) and about 0.001% (w/v), most preferably about 0.1% (w/v) or less.

As a further preferred aspect of this embodiment of the invention, the 5-bromo-6-(2-imidozolin-2-ylamino) quinoxaline, or salt thereof, is in aqueous solution at a pH of greater than about 7.0 at room temperature or about 7.2 or greater at room temperature, even more preferably about 7.5 or greater at room temperature, most preferably at about 7.7 or greater at room temperature.

In another embodiment, the alpha-2-adrenergic agonist components in the present compositions are made more soluble, particularly at neutral to alkaline pH values, and may be more effectively utilized as therapeutic agents. The SECs employed in the present compositions may be effective in the solubilization of charged alpha-2-adrenergic agonist components, uncharged alpha-2-adrenergic agonist components or both. The present compositions include liquid carrier components and have the characteristics of liquid, for example, aqueous liquid, solutions.

Alpha-2-adrenergic agonist components have a stimulatory activity directed towards at least one of the alpha 2 receptor subtypes alpha 2A, alpha 2B or alpha 2C. Preferably, the activity at such subtype(s) is at least 10 fold greater than at any alpha 1 adrenergic receptor subtype. Even more preferably, the activity at an alpha 2 receptor is at least 50 fold greater, or at least 100 fold greater or at least 1000 fold greater than at any alpha 1 receptor. Exemplary alpha-2-agonists include, without limitation, xylazine, detomidine, medetomidine, clonidine, brimonidine, tizanidine, lofexidine, guanfacine, guanabenz acetate, and dexmedetomidine.

The alpha-2-adrenergic agonist components are soluble in the present compositions at pH values greater than 7. In one embodiment, the present concentrations contain the alpha adrenergic agonist components at or nearly at their aqueous solubility limit at room temperature and maintain comparable efficacy to higher concentrations of the alpha adrenergic agonist components in a similar composition at a pH of 7 or below.

In one preferred embodiment, the alpha-2-adrenergic agonist components are combined with at least one SEC in the presently claimed compositions, and therefore have increased solubility in the present compositions at pH values greater than 7, such as, without limitation, about pH 7.2, about pH 7.4, about pH 7.7, and about pH 8.0, as compared to identical alpha-2-adrenergic agonist components, at comparable concentrations, in compositions lacking the SECS.

A preferred composition comprises about 0.1% (w/v) brimonidine at a pH about 7.7. Even more preferably, such a composition also comprises an SEC. The SEC may be selected from any SEC, but preferred SECs include carboxymethyl cellulose, polyvinyl alcohol, or polyvinyl pyrrolidone.

In another embodiment, the alpha-2-adrenergic agonist components have increased solubility in the present compositions at pH values in the range of about 7 to about 10 and, as compared to identical alpha-2-adrenergic agonist components in similar compositions, at comparable concentrations, without the SECs. Even more preferably the alpha-2-adrenergic agonist components in the compositions of the present invention have such increased solubility at pH values of above about 7.0, preferably between about pH 7.0 and about pH 8.5, more preferably between about 7.2 and about 8.2, even more preferably between about 7.5 and about 8.0, or at about pH 7.7.

Without wishing to be limited by any theory or mechanism of operation, it is believed that solubilized alpha-2-adrenergic agonist components are better able to cross lipid membranes relative to unsolubilized alpha-2-adrenergic agonist components. Moreover, it is also believed that an uncharged alpha-2-adrenergic agonist component is better able to cross a lipid membrane than one which is charged.

In one embodiment, the SECs are capable of solubilizing the alpha-2-adrenergic agonist components in the biological environments into which they are introduced at therapeutically effective concentrations. Preferably, the biological environments into which the present compositions are introduced have pH values ranging from about 7 to about 9. For example, a composition comprising a SEC and an alpha-2-adrenergic agonist component may be topically administered to the surface of an eye, which has a pH of about 7, wherein the alpha-2-adrenergic agonist component is substantially soluble at the administered area. Furthermore, the soluble alpha-2-adrenergic agonist components at the administered area will diffuse more readily through biological lipid membranes than alpha-2-adrenergic agonist components which are not soluble, whether in the presence of SECs or otherwise. Maintaining solubility of alpha-2-adrenergic agonist components in aqueous solution preferably reduces irritation to sensitive tissues in contact or interacting with the alpha-2-adrenergic agonist components.

Of course, the soluble alpha-2-adrenergic agonist components in the compositions hereby disclosed and claimed must be capable of being delivered at a therapeutically effective concentration. While it is clearly possible to make a solution containing vanishingly small concentrations of soluble alpha-2-adrenergic agonist components, such a solution is not therapeutically useful unless it is effective to confer a benefit to the mammal who receives it. Preferably, the current compositions are capable of delivering a therapeutic effect substantially equal to, or greater than, that provided by a formulation of the same alpha-2-adrenergic agonist component at a pH less than 7.0. Even more preferably, the current compositions are capable of delivering a therapeutic effect substantially equal to, or greater than, that provided by a formulation of the same alpha-2-adrenergic agonist component at a pH less than 7.0, and at a lower concentration of the active agent than in the lower pH formulation.

In one preferred embodiment the presently useful alpha-2-adrenergic agonist components are chosen to benefit from and be stabilized or solubilized by the presence of the SECs. In this embodiment, the alpha-2-adrenergic agonist components are provided with increased apparent solubility preferably increased apparent water solubility, by the presence of the SECs.

Examples of alpha-2-adrenergic agonist components include molecules containing amines. Preferably, the alpha-2-adrenergic agonist components are amine-containing molecules with pKa's of greater than about 7, more preferably about 7 to about 9.

Alpha-2-adrenergic agonist components include alpha-2-adrenergic agonists. As used herein, the term alpha-2 adrenergic agonist includes chemical entities, such as compounds, salts, esters, ions, complexes and the like, that bind to, and activate, one or more of the alpha 2 A adrenergic receptor, the alpha 2B adrenergic receptor and alpha 2C adrenergic receptor. When stimulated, these G-protein coupled receptors perform a number of cell signaling functions; one or more may be involved in, for example, inhibiting the presynaptic release of the neurotransmitter norepinephrine. While not wishing to be bound by theory, it is thought that stimulation of one or more of the alpha 2 receptor subtypes results in the suppression of calcium influx into the target neuron, thus inhibiting neurotransmitter release. This inhibition of norepinephrine in presynaptic neurons appears to be involved in analgesia by inhibiting the generation or propagation of the pain response.

While the alpha 2 receptors are found predominantly in a presynaptic site, alpha 2 receptors can also be found in post- and extrasynaptic locations and in peripheral and CNS neurons.

The alpha-2 adrenergic agonists of the invention bind to the alpha-2 adrenergic receptors, and are able to cause a decrease or inhibition of the release of neuronal norepinephrine at the presynaptic sites in affected cells. Additionally, they may work on alpha-2 adrenergic receptors postsynaptically, for example, by inhibiting beta-adrenergic receptor-stimulated formation of cyclic AMP.

Alpha-2 adrenergic agonists also include compounds that have neuroprotective activity. For example, 5-bromo-6-(2-imidozolin-2-ylamino) quinoxaline is an alpha-2-adrenergic agonist which has a neuroprotective activity. The mechanism or neuroprotection is still not completely known.

Without limiting the invention to the specific groups and compounds listed, the following is a list of representative alpha-2 adrenergic agonists useful in this invention: imino-imidazolines, including clonidine, apraclonidine; imidazolines, including naphazoline, xymetazoline, tetrahydrozoline, and tramazoline; imidazoles, including detomidine, medetomidine, and dexmedetomidine; azepines, including B-HT 920 (6-allyl-2-amino-5,6,7,8 tetrahydro-4H-thiazolo [4,5-d]-azepine and B-HT 933; thiazines, including xylazine; oxazolines, including rilmenidine; guanidines, including guanabenz and guanfacine; catecholamines; and the like and esters, salts and derivatives thereof.

Particularly useful alpha-2-adrenergic agonists include quinoxaline components. In one embodiment, the quinoxaline components include quinoxaline, derivatives thereof and mixtures thereof. Preferably, the derivatives of quinoxaline include (2-imidozolin-2-ylamino) quinoxaline. More preferably, the derivatives of quinoxaline include 5-halide-6-(2-imidozolin-2-ylamino) quinoxaline. The "halide" of the 5-halide-6-(2-imidozolin-2-ylamino) quinoxaline may be a fluorine, a chlorine, an iodine, or preferably, a bromine, to form 5-bromo-6-(2-imidozolin-2-ylamino) quinoxaline. Even more preferably, the derivatives of quinoxaline to be used in accordance with this invention include a tartrate of 5-bromo-6-(2-imidozolin-2-ylamino) quinoxaline, or brimonidine tartrate.

Other useful quinoxaline derivatives are well known. For example, useful derivatives of a quinoxaline include the ones disclose by Burke et al U.S. Pat. No. 5,703,077. See also Danielwicz et al U.S. Pat. No. 3,890,319. Each of the disclosures of Burke et al and Danielwicz et al is incorporated in its entirety by reference herein.

The quinoxalines and derivatives thereof, for example brimonidine tartrate, are amine-containing and preferably have pKa's of greater than 7, preferably about 7.5 to 9.

Analogs of the foregoing compounds that function as alpha-2 adrenergic agonists also are specifically intended to be embraced by the invention.

Preferably, the alpha-2-adrenergic agonists of the present invention, are effective in activating alpha-2A-adrenergic receptors, alpha-2B-adrenergic receptors and/or alpha-2C adrenergic receptors.

In one embodiment, the alpha-2-adrenergic agonist components are at least about 30% uncharged in the presently disclosed and claimed compositions, preferably at least about 50% uncharged. Those of skill in the art will appreciate that the pKa is the negative log of the ionization constant (or the pH at which the compound is 50% ionized), and that a reference in this application to a specific percent of the compound uncharged (such as, for example, at least 30% or 50% uncharged) is intended to refer to the compound on a stoichiometric basis.

Preferably, the soluble alpha-2-adrenergic agonist components of the present formulations are at least about 30% uncharged, or at least about 50% uncharged in the biological environment into which the compositions are administered.

Without wishing to be limited by any theory or mechanism of action, it is believed that the uncharged forms of the present alpha 2 adrenergic compounds facilitate their permeability across membrane lipid bilayers.

In those embodiments involving an SEC, any suitable SEC (or combination of SECs) may be employed in accordance with the present invention. In one embodiment, the SECs include uncharged SECs, such as, without limitation, pyrrolidone components, polyvinyl alcohol (PVA), uncharged cellulose derivatives, Pemulin, carbomers, Carbopols and the like. Examples of pyrrolidone components are polyvinylpyrrolidones (povidone) and derivatives thereof. In a further embodiment, the SECs include polyanionic components. The useful polyanionic components include, but are not limited to, those materials which are effective in increasing the apparent solubility, preferably water solubility, of poorly soluble alpha-2-adrenergic agonist components and/or enhance the stability of the alpha-2-adrenergic agonist components and/or reduce unwanted side effects of the alpha-2-adrenergic agonist components. Furthermore, the polyanionic component is preferably ophthalmically acceptable for topical treatment at the concentrations used. Additionally, the polyanionic component preferably includes three (3) or more anionic (or negative) charges. In the event that the polyanionic component is a polymeric material, it is preferred that each of the repeating units of the polymeric material include a discrete anionic charge. Particularly useful anionic components are those which are water soluble, for example, soluble at the concentrations and pH values used in the presently useful liquid aqueous media, such as a liquid aqueous medium containing the alpha-2-adrenergic components.

The polyanionic component is preferably sufficiently anionic to form an ionic or other electrostatic interaction with those charged or polar moieties of the alpha-2-adrenergic agonist component. Such interaction is believed to be desirable to solubilize certain formulations of the alpha-2-adrenergic agonist component and/or to maintain such alpha-2-adrenergic agonist component soluble in the carrier component, for example a liquid medium.

Polyanionic components also include one or more polymeric materials having multiple anionic charges. Examples include:
    metal carboxymethylstarchs
    metal carboxymethylhydroxyethylstarchs
    hydrolyzed polyacrylamides and polyacrylonitriles heparin
    homopolymers and copolymers of one or more of:
        acrylic and methacrylic acids
        metal acrylates and methacrylates
        alginic acid
        metal alginates
        vinylsulfonic acid
        metal vinylsulfonate amino acids, such as aspartic acid, glutamic acid and the like
metal salts of amino acids
p-styrenesulfonic acid
metal p-styrenesulfonate 2-methacryloyloxyethylsulfonic acids
metal 2-methacryloyloxethylsulfonates 3-methacryloyloxy-2-hydroxypropylsulonic acids
metal 3-methacryloyloxy-2-hydroxypropylsulfonates 2-acrylamido-2-methylpropanesulfonic acids
metal 2-acrylamido-2-methylpropanesulfonates allylsulfonic acid
metal allylsulfonate and the like.

By "metal" is meant alkali and alkaline earth metals such as Na, K, Ca and the like.

In another embodiment, the polyanionic components include anionic polysaccharides which tend to exist in ionized forms at higher pHs, for example, pH's of about 7 or higher. The following are some examples of anionic polysaccharides which may be employed in accordance with this invention.

Polydextrose is a randomly bonded condensation polymer of dextrose which is only partially metabolized by mammals. The polymer can contain a minor amount of bound sorbitol, citric acid, and glucose. Chondroitin sulfate also known as sodium chondroitin sulfate is a mucopolysaccharide found in every part of human tissue, specifically cartilage, bones, tendons, ligaments, and vascular walls. This polysaccharide has been extracted and purified from the cartilage of sharks. Carrageenan is a linear polysaccharide having repeating galactose units and 3,6 anhydrogalactose units, both of which can be sulfated or nonsulfated, joined by alternating 1-3 and beta 1-4 glycosidic linkages. Carrageenan is a hydrocolloid which is heat extracted from several species of red seaweed and irish moss. Maltodextrins are water soluble glucose polymers which are formed by the reaction of starch with an acid and/or enzymes in the presence of water.

Other anionic polysaccharides found useful in the present invention are hydrophilic colloidal materials and include the natural gums such as gellan gum, alginate gums, i.e., the ammonium and alkali metal salts of alginic acid and mixtures thereof. In addition, chitosan, which is the common name for deacetylated chitin, is useful. Chitin is a natural product comprising poly-(N-acetyl-D-glucosamine). Gellan gum is produced from the fermentation of *Pseudomonas elodea* to yield an extracellular heteropolysaccharide. The alginates and chitosan are available as dry powders from, e.g., Protan, Inc., Commack, N.Y. Gellan gum can be purchased from, e.g., the Kelco Division of Merk & Co., Inc., San Diego, Calif.

Generally, the alginates can be any of the water-soluble alginates including the alkali metal alginates, such as sodium, potassium, lithium, rubidium and cesium salts of alginic acid, as well as the ammonium salt, and the soluble alginates of an organic base such as mono-, di-, or tri-ethanolamine alginates, aniline alginates, and the like. Generally, about 0.2% to about 1% by weight and, preferably, about 0.5% to about 3.0% by weight of gellan, alginate or chitosan ionic polysaccharides, based upon the total weight of the composition, are used to obtain the gel compositions of the invention.

In one embodiment, the anionic polysaccharides are cyclized. More preferably, the cyclized anionic polysaccharides include less than ten monomer units. Even more preferably, the cyclized polysaccharides include less than six monomer units.

A particularly useful group of cyclized anionic polysaccharides includes the cyclodextrins. Examples of the cyclodextrin group include, but are not limited to: α-cyclodextrin, derivatives of α-cyclodextrin, β-cyclodextrin, derivatives of β-cyclodextrin, γ-cyclodextrin, derivatives of γ-cyclodextrin, carboxymethyl-β-cyclodextrin, carboxymethyl-ethyl-β-cyclodextrin, diethyl-β-cyclodextrin, dimethyl-β-cyclodextrin, methyl-β-cyclodextrin, random methyl-β-cyclodextrin, glucosyl-β-cyclodextrin, maltosyl-β-cyclodextrin, hydroxyethyl-β-cyclodextrin, hydroxypropyl-β-cyclodextrin, sulfobutylether-β-cyclodextrin, and the like and mixtures thereof. Sulfobutylether-β-cyclodextrin is a preferred cyclized anionic polysaccharide in accordance with the present invention. It is advantageous that the SECs employed in this invention, including the above mentioned cyclodextrins, be formulated at so as to be non-toxic to the mammal (including to humans) at the concentration employed.

As used herein, the term "derivative(s)", as it relates to a cyclodextrin, means any substituted or otherwise modified compound which has the characteristic chemical structure of a cyclodextrin sufficiently to function as a cyclodextrin component, for example, to enhance the solubility and/or stability of active components and/or reduce unwanted side effects of the active components and/or to form inclusive complexes with active components, as described herein.

Although cyclodextrins and/or their derivatives may be employed as SECs, one embodiment of the invention may include SECs other than cyclodextrins and/or their derivatives.

A particularly useful and preferred class of polyanionic component includes anionic cellulose derivatives. Anionic cellulose derivatives include metal carboxymethyl celluloses, metal carboxymethyl hydroxyethyl celluloses and hydroxypropyl methyl celluloses and derivatives thereof.

The present polyanionic components often can exist in the uncharged state, for example in the solid state, in combination with a counter ion; in particular, a plurality of discrete cations approximately equal in number to the number of discrete anionic charges of the SEC so that the polyanionic component is electrically neutral when it possesses a charge.

Since the polyanionic components are preferably ophthalmically acceptable, it is preferred that the metal associated with the unionized polyanionic component be ophthalmically acceptable in the concentrations used. Particularly useful metals include the alkali metals, for example, sodium and potassium, the alkaline earth metals, for example, calcium and magnesium, and mixtures thereof.

Sodium is a very useful metal capable of acting as a counter ion in the unionized polyanionic component. Polyanionic components which, in the unionized states, are combined with cations other than $H^+$ and metal cations can be employed in the present invention.

In those embodiments of the present invention that involve the use of SECs, the amount of SEC is not of critical importance so long as solubility at the alpha-2-adrenergic agonist component is at least somewhat increased and is present in a biologically acceptable amount. Such amount should be effective to perform the desired function or functions in the present composition and/or after administration to the human or animal. In one embodiment, the amount of SEC, preferably the polyanionic component, is sufficient to assist in solubilizing a major amount, and more preferably substantially all, of the alpha-2-adrenergic agonist component in the present composition. In one useful embodiment, the amount of polyanionic component in the present composition is in the range of about 0.1% to about 30% (w/v) or more of the composition. Preferably, the amount of polyanionic component is in the range of about 0.2% (w/v) to about 10% (w/v). More preferably, the amount of polyanionic component is in the range of about 0.2% (w/v) to about 0.6% (w/v).

Even more preferably, the polyanionic component is carboxymethylcellulose and is present in the composition in the range of about 0.2% (w/v) to about 0.6% (w/v). A particularly useful concentration of carboxymethylcellulose in the present compositions is about 0.5%.

In one embodiment, the SECs, for example a carboxymethylcellulose, assist in solubilizing the alpha-2-adrenergic agonist components in the compositions. Although the SECs are capable of aiding in the solubilization of ionized alpha-2-adrenergic agonist components, it is preferable that SECs used in this aspect of the invention assist in the solubilization of alpha-2-adrenergic agonist components at neutral or alkaline pH. For example, in one embodiment, carboxymethylcellulose may help solubilize ionized alpha-2-adrenergic agonist components. In another embodiment, carboxymethylcellulose may help solubilize substantially uncharged population of alpha-2-adrenergic agonist components. In a preferred embodiment, the carboxymethylcellulose helps solubilize ionized brimonidine tartrate in the compositions. More preferably, the carboxymethylcellulose helps solubilize a substantially uncharged population of brimonidine tartrate in the compositions.

The compositions of the present invention may also include preservative components or components which assist in the preservation of the composition. In a preferred embodiment the claimed compositions contains at least one preservative component selected so as to be effective and efficacious as preservatives in the present compositions, that is in the presence of polyanionic components, and preferably have reduced toxicity and more preferably substantially no toxicity when the compositions are administered to a human or animal.

Preferably, the present preservative components or components which assist in the preservation of the composition, preferably the alpha-2-adrenergic agonist components therein, are effective in concentrations of less than about 1% (w/v) or about 0.8% (w/v) and may be 500 ppm (w/v) or less, for example, in the range of about 10 ppm (w/v) or less to about 200 ppm (w/v). Preservative components in accordance with the present invention preferably include, but are not limited to, those which form complexes with the polyanionic component to a lesser extent than does benzalkonium chloride.

Very useful examples of the present preservative components include, but are not limited to oxidative preservative components, for example and without limitation, oxidative preservatives such as oxy-chloro and oxy-borate components, peroxides, persalts, peracids, and the like, and mixtures thereof. Specific examples of oxy-chloro components useful as preservatives in accordance with the present invention include hypochlorite components, for example hypochlorites; chlorate components, for example chlorates; perchlorate components, for example perchlorates; and chlorite components. Examples of chlorite components include stabilized chlorine dioxide (SCD), metal chlorites, such as alkali metal and alkaline earth metal chlorites, and the like and mixtures therefor. Technical grade (or USP grade) sodium chlorite is a very useful preservative component. The exact chemical composition of many chlorite components, for example, SCD, is not completely understood. The manufacture or production of certain chlorite components is described in McNicholas U.S. Pat. No. 3,278,447, which is incorporated in its entirety herein by reference. Specific examples of useful SCD products include that sold under the trademark Dura Klor by Rio Linda Chemical Company, Inc., and that sold under the trademark Anthium Dioxide by International Dioxide, Inc. An especially useful SCD is a product sold under the trademark Purite™ by Allergan, Inc.

Other examples of oxidative preservative components includes peroxy components. For example, trace amounts of peroxy components stabilized with a hydrogen peroxide stabilizer, such as diethylene triamine penta(methylene phosphonic acid) or 1-hydroxyethylidene-1,1-diphosphonic acid, may be utilized as a preservative for use in components designed to be used in the ocular environment. Also, virtually any peroxy component may be used so long as it is hydrolyzed in water to produce hydrogen peroxide. Examples of such sources of hydrogen peroxide, which provide an effective resultant amount of hydrogen peroxide, include sodium perborate decahydrate, sodium peroxide and urea peroxide. It has been found that peracetic acid, an organic peroxy compound, may not be stabilized utilizing the present system. See, for example, Martin et al U.S. Pat. No. 5,725,887, the disclosure of which is incorporated in its entirety herein by reference.

Preservatives other than oxidative preservative components may be included in the compositions. The choice of preservatives may depend on the route of administration. Preservatives suitable for compositions to be administered by one route may possess detrimental properties which preclude their administration by another route. For nasal and ophthalmic compositions, preferred preservatives include, without limitation, quaternary ammonium compounds, in particular the mixture of alkyl benzyl dimethyl ammonium compounds and the like known generically as "benzalkonium chloride", the mixture comprising decyltrimethylmmonium bromide, dodecyltrimethylmmonium bromide and tetradecyltrimethylmmonium bromide termed "cetrimide", BDB, and the preservative polyquaternium-1 (marketed under the trade name Polyquad®), and biguanide preservatives, such as polyhexamethylene biguanide ("PHMB").

For compositions to be administered by inhalation, however, the preferred preservative is chlorbutol and the like. Other preservatives which may be used, especially for compositions to be administered rectally, include alkyl esters of p-hydroxybenzoic acid and mixtures thereof, such as the mixture of methyl, ethyl, propyl, butyl esters and the like which is sold under the trade name "Nipastat."

In another broad aspect of the present invention, compositions are provided which comprise an alpha-2-adrenergic agonist component, a preservative component in an effective amount to at least aid in preserving, preferably in an amount effective to preserve, the compositions and a liquid carrier component. Preferably, the preservative components include oxy-chloro components, or PHMB. Such compounds must be effective at preventing the growth of gram positive bacteria, gram negative bacteria, or fungi and preferably be such that they (1) do not substantially or significantly detrimentally affect the alpha-2-adrenergic agonist components in the compositions or the patients to whom the compositions are administered, and (2) are substantially biologically acceptable and chemically stable. Such compositions in accordance with the present invention comprise an alpha-2-adrenergic agonist component, an oxy-chloro component, a quaternary ammonium compound, or a biguanide such as PHMB, and a liquid carrier component, and preferably are substantially free of cyclodextrins.

The carrier components useful in the present invention are selected to be non-toxic and have no substantial detrimental effect on the present compositions, on the use of the compositions or on the human or animal to whom the compositions are administered.

In one embodiment, the carrier component is a liquid carrier. In a preferred embodiment, the carrier component is a liquid aqueous carrier component. A particularly useful aqueous liquid carrier component is that derived from saline, for example, a conventional saline solution or a conventional buffered saline solution. The aqueous liquid carrier preferably has a pH in the range of about 6 to about 9 or about 10, more preferably about 6 to about 8, and still more preferably about 7.5. The liquid medium preferably has an ophthalmically acceptable tonicity level, for example, of at least about 200 mOsmol/kg, more preferably in the range of about 200 to about 400 mOsmol/kg. In an especially useful embodiment, the osmolality or tonicity of the carrier component is substantially isotonic with reference to the tonicity of the fluids of the surface of the eye, in particular the human eye.

In one embodiment, the carrier components containing the SECs and the alpha-2-adrenergic agonist components may have viscosities of more than about 0.01 centipoise (cps) at 25° C., preferably more than about 1 cps at 25° C., even more preferably more than about 10 cps at 25° C. In a preferred embodiment, the composition has a viscosity of about 50 cps at 25° C. and comprises a conventional buffer saline solution, a carboxymethylcellulose and brimonidine tartrate.

In order to insure that the pH of the aqueous liquid carrier component, and thus the pH of the composition, is maintained within the desired range, the aqueous liquid carrier component may include at least one buffer component. Although any suitable buffer component may be employed, it is preferred to select a buffer not capable of evolving a significant amount of gas, such as chlorine dioxide or $CO_2$. It is preferred that the buffer component be inorganic. Alkali metal and alkaline earth metal salt buffer components are advantageously used in the present invention.

Any suitable ophthalmically acceptable tonicity adjusting component may be employed, provided that such component or components are compatible with the other ingredients of the liquid aqueous carrier component and do not have deleterious or toxic properties which could harm the human or animal to whom the present compositions are administered. Examples of useful tonicity components include sodium chloride, potassium chloride, mannitol, dextrose, glycerin, propylene glycol and mixtures thereof. In one embodiment, the tonicity component is selected from inorganic salts and mixtures thereof.

The present compositions may conveniently be presented as solutions or suspensions in aqueous liquids or non-aqueous liquids, or as oil-in-water or water-in-oil liquid emulsions. The present compositions may include one or more additional ingredients such as diluents, flavoring agents, surface active agents, thickeners, lubricants, and the like, for example, such additional ingredients which are conventionally employed in compositions of the same general type.

The present compositions, if in the form of aqueous suspensions, may include excipients suitable for the manufacture of aqueous suspensions. Such excipients are suspending agents, without limitation including sodium alginate, gum tragacanth and gum acacia. Dispersing or wetting agents may include a naturally occurring phosphatide, for example, lecithin, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol mono-oleate, or condensation products of ethylene oxide with partial esters derived from fatty acids and hexitol anhydrides, for example, polyoxyethylene sorbitan mono-oleate, and the like and mixtures thereof. Aqueous suspensions of this aspect of the present invention may also contain one or more coloring agents, one or more flavoring agents and one or more sweetening agents, such as sucrose, saccharin, and the like and mixtures thereof.

If the present compositions are in the form of oily suspensions they may be formulated in a vegetable oil, for example, olive oil, sesame oil or coconut oil, or in a mineral oil such as liquid paraffin. Such suspensions may contain a thickening agent, for example beeswax, hard paraffin or cetyl alcohol. Sweetening agents, such as those set forth above, and flavoring agents may be added to provide a palatable oral preparation.

The present compositions may alternatively be in the form of oil-in-water emulsions. The oily phase may be a vegetable oil, for example, olive oil or arachis oil, or a mineral oil, for example, liquid paraffin, and the like and mixtures thereof. Suitable emulsifying agents may be naturally-occurring gums, for example, gum acacia or gun tragacanth, naturally-occurring phosphatides, for example, soya bean lecithin, and esters or partial esters derived from fatty acids and hexitol anhydrides, for example, sorbitan mono-oleate, and condensation products of the said partial esters with ethylene oxide, for example, polyoxyethylene sorbitan mono-oleate. The emulsions may also contain sweetening and flavoring agents.

The present compositions, if in the form of syrups and elixirs, may be formulated with sweetening agents, for example, as described elsewhere herein. Such formulations may also contain a demulcent, and flavoring and coloring agents.

The specific dose level for any particular human or animal depends upon a variety of factors including the activity of the active component employed, the age, body weight, general health, sex, diet, time of administration, pH of the formulation, route of administration, rate of excretion, drug combination and the severity of the particular condition undergoing therapy. For 5-bromo-6-(2-imidozolin-2-ylamino) quinoxaline, a therapeutically effective dose in the present compositions is delivered at a concentration of less than 0.2% (w/v), such as about 0.15% (w/v) or about 0.1% (w/v) or less. The pH of such compositions is greater than 7.0; in one aspect the dose is about 0.15% and the pH is about 7.2; in another aspect the dose is about 0.1% and the pH is about 7.7.

In one aspect of the invention, complexes are formed in the present compositions. In one embodiment, the complexes include at least one monomer unit of a quinoxaline component. Examples of quinoxaline components include quinoxaline, (2-imidozolin-2-ylamino) quinoxaline, 5-bromo-6-(2-imidozolin-2-ylamino) quinoxaline, salts thereof, esters thereof, other derivatives thereof, and the like and mixtures thereof. For example, in one embodiment, a complex of the present invention may include a conjugation of 5-bromo-6-(2-imidozolin-2-ylamino) quinoxaline monomer units. In another embodiment, the complex may include a conjugation of 5-bromo-6-(2-imidozolin-2-ylamino) quinoxaline monomer units and brimonidine tartrate monomer units.

In a preferred embodiment of this aspect, the complexes of the present invention are dimers. For example, a dimer in accordance with the present invention may include a quinoxaline and a 5-bromo-6-(2-imidozolin-2-ylamino) quinoxaline. Preferably, a dimer in accordance with the present invention includes two trimonidine tartrate monomer units.

Without wishing to limit this aspect of the invention to any theory or mechanism of operation, it is believed that a peroxide forming agent or strong oxidizing agent such as the oxidative preservative components, for example oxy-chloro components, peroxides, persalts, peracids, and the like, and mixtures thereof may facilitate the formation of the complexes, preferably complexes of alpha-2-adrenergic agonist components. For example, dimers of brimonidine tartrate monomer units are believed to be formed in the presence of chlorites, preferably stabilized chlorine dioxide.

Furthermore, it is believed that the interactions between the monomers which serve to hold the monomers or monomer subunits together to form a complex, preferably an oligomer and more preferably a dimer, may include, but not limited to, covalent bonding, ionic bonding, hydrophobic bonding, electrostatic bonding, hydrogen bonding, other chemical and/or physical interactions, and the like and combinations thereof. Such complexes may disassociate in liquid, for example, aqueous liquid, media. In one embodiment, the monomers or monomer subunits are held together by other than covalent bonding. In one embodiment, the monomers or monomer subunits are held together by electrostatic bonding or forces.

The following non-limiting examples illustrate certain aspects of the present invention.

Example 1

Brimonidine tartrate has a pKa of about 7.78. The pH-solubility profile of brimonidine tartrate in an aqueous formulation (Ophthalmic Solution) was established in the pH range of about 5 to about 8 at 23° C. Table 1. It will be understood that concentrations of adrenergic agonists other than those shown may be used in the compositions of the present invention, so long as they have therapeutic activity. Likewise, the temperature may be varied somewhat, for example, solubility curves may be performed at room temperature.

The formulation vehicle was prepared by first dissolving polyvinyl alcohol (PVA) in water. The PVA was added to approximately ⅓ of the required total amount of purified water with constant stirring. The slurry was stirred for 20-30 minutes and then heated to 80-95° C. with constant stirring. The mixture was removed from the heat source within 1 hour after having reached the temperature of 80-90° C. and stirred for an additional 10 minutes to ensure homogeneity (Part I). The other ingredients of the Ophthalmic Solution, except for brimonidine tartrate, were dissolved in a separate container with an additional ⅓ of the required total amount of purified water (Part II). The PVA mixture (Part I) was then quantitatively transferred to Part II using several rinse volumes of purified water. The solution was adjusted to final volume with purified water without pH adjustment.

Brimonidine tartrate was weighed and transferred to a 10 mL test tube containing 5 mL of the formulation vehicle described above. The pH of each sample was then adjusted to a desired value using dilute sodium hydroxide and/or dilute hydrochloric acid. The samples were placed in a rack on a stir plate and stirred at high speed to achieve uniform mixing for 2 days; a partition was placed between the rack and the stir plate to prevent any heat diffusion from the stir plate to the samples. The temperature of the laboratory was monitored throughout the study and was found to be 23±1° C.

At the end of two days of stirring, the pH value of each sample was measured, and then approximately 1 mL of each sample was placed in a micro centrifuge tube (polypropylene) and centrifuged at 4,000 rpm for 10 minutes. The supernatant was filtered through a 1 μm filter unit (Whatman, 13 mm, PTFE). The first 3-4 drops of the filtrate were discarded; the rest of the filtrate was received and diluted quantitatively with HPLC mobile phase. The dilute sample was then injected directly on the HPLC column (Dupont Zorbax, 250 mm×4.6 mm, 5 μm) for brimonidine tartrate assay in order to quantify the amount of brimonidine tartrate. A control of 0.5% brimonidine tartrate was prepared in the same formulation vehicle at pH 6.3-6.5 and assayed before (untreated) and after (treated) centrifugation and filtration. This was done to evaluate the potential loss of brimonidine tartrate in these two steps of the sample preparation. To ensure reproducibility, the study was repeated on consecutive days.

TABLE I 0.5% Brimonidine tartrate in Ophthalmic Solution.

| Ingredient | Percent (w/v) |
|---|---|
| Brimonidine tartrate | 0.50 |
| Benzalkonium Chloride, NF | 0.0050 |
| Polyvinyl Alcohol, USP | 1.4 |
| Sodium Chloride, USP | 0.66 |
| Sodium Citrate, dihydrate, USP | 0.45 |
| Hydrochloric Acid, NF or Sodium Hydroxide, NF for pH adjustment | 5-8 |
| Purified Water, USP | QS |

The solubility data for brimonidine tartrate in the formulation vehicles are presented in Table II. The results show that the solubility of brimonidine tartrate is highly pH-dependent and spans more than two orders of magnitude over the pH range of 5-8. The solubility decreases sharply as the pH increases. The results for the treated and untreated controls are very close, suggesting that centrifugation and filtration does not cause any significant loss of brimonidine tartrate. The two solubility profiles obtained on consecutive days agree with each other.

TABLE II

Solubility Of Brimonidine Tartrate In The Ophthalmic Solution Over pH Range Of 5 To 8.

| | STUDY 1 | | STUDY 2 | |
|---|---|---|---|---|
| Sample | pH$^a$ | Solubility$^e$ | pH$^a$ | Solubility$^e$ |
| 1 | 5.55> | 16.44$^b$ | 5.50> | 20.06$^b$ |
| 2 | 5.92 | 13.26 | 5.92 | 16.08 |
| 3 | 6.14 | 3.04 | 6.06 | 5.01 |
| 4 | 6.57 | 0.755 | 6.90 | 0.319 |
| 5 | 7.00 | 0.269 | 7.40 | 0.119 |
| 6 | 7.45 | 0.117 | 7.77 | 0.063 |
| 7 | 7.83 | 0.062 | 7.86 | 0.058 |
| 8 | — | — | 7.88 | 0.054 |
| Control/ (untreated) | — | 0.486$^c$ | — | — |
| Control/ (treated) | — | 0.484$^d$ | — | — |

$^a$Measured after stirring for two-days before sample withdrawal for centrifugation and filtration.
$^b$Represents theoretical concentration based on sample weight. The sample solution was clear indicating that all of the brimonidine tartrate had dissolved.
$^c$Concentration of brimonidine tartrate in control before centrifugation and filtration step.
$^d$Concentration of brimonidine tartrate in control after centrifugation and filtration step.
$^e$mgml$^{-1}$ Example 2

The effect of pH on the solubility of brimonidine tartrate in liquid formulations with and without SECs was determined. Particularly, the effect of the presence or absence of various concentrations of an exemplary SEC, sodium carboxymethylcellulose (CMC), on the solubility of brimonidine tartrate at various pH conditions was determined. The various concentrations of CMC tested with Brimonidine tartrate were 0%, 0.056%, 0.17%, 0.5%, 1.5% (w/v), see Table III.

The samples tested also contained isotonic components, buffer components, and stabilized chlorine dioxide (Purite™), Table III. Sodium carboxymethylcellulose, sodium chloride, potassium chloride, calcium chloride dihydrate, and magnesium chloride hexahydrate were USP grade. Boric acid and sodium borate decahydrate were NF grade.

TABLE III

|  | Sample 1 | Sample 2 | Sample 3 | Sample 4 | Sample 5 |  |
| --- | --- | --- | --- | --- | --- | --- |
| Brimonidine tartrate | 0.2% | 0.2% | 0.2% | 0.2% | 0.2% | (w/v) |
| CMC | 0.0% | 0.056% | 0.17% | 0.5% | 1.5% | (w/v) |
| Stabilized chlorine dioxide[a] | 0.005% | 0.005% | 0.005% | 0.005% | 0.005% | (w/v) |
| Sodium chloride | 0.58% | 0.58% | 0.58% | 0.58% | 0.58% | (w/v) |
| Potassium chloride | 0.14% | 0.14% | 0.14% | 0.14% | 0.14% | (w/v) |
| Calcium chloride, dihydrate | 0.02% | 0.02% | 0.02% | 0.02% | 0.02% | (w/v) |
| magnesium chloride, hexahydrate | 0.006% | 0.006% | 0.006% | 0.006% | 0.006% | (w/v) |
| boric acid | 0.2% | 0.2% | 0.2% | 0.2% | 0.2% | (w/v) |
| sodium tetraborate, decahydrate | 0.14% | 0.14% | 0.14% | 0.14% | 0.14% | (w/v) |

[a] Sold under the trademark Purite ™ by Allergan, Inc.

Each sample (1 through 5) was brought to various points within a range of pH values from about 7 to about 10. The vials containing the sample solutions were placed on a laboratory rotator and left to equilibrate for fifteen days at 21° C. The sample solutions were filtered using a 25 mm diameter polysulfone cellulose acetate syringe type filter with 0.45 μm pore size. The filtered solutions were assayed for the amount of brimonidine tartrate in solution.

Conventional HPLC and detection techniques were used to detect and determine the concentrations of soluble brimonidine tartrate. See Table IV. Solubility is plotted against pH for each CMC concentration. The experimental data points were fitted to a modified Henderson-Hasselbalch equation using a nonlinear least squares routine (Deltagraph version 4.0 DeltaPoint, Inc.), See FIG. 1. The $R^2$ values show the statistical fit between the experimental values and the theoretical equation to be greater than 0.991.

TABLE IV

| | Solubility of Brimonidine tartrate (% w/v) | | | | |
| --- | --- | --- | --- | --- | --- |
| pH | 0% CMC | 0.056% CMC | 0.17% CMC | 0.5% CMC | 1.5% CMC |
| 6.67 |  | 0.9302 |  | 1.4464 |  |
| 6.68 |  |  | 1.4200 |  | 1.4256 |
| 6.93 |  |  | 0.7302 |  |  |
| 7.10 |  |  |  | 0.3693 |  |
| 7.11 | 0.2064 | 0.2828 |  |  |  |
| 7.35 |  |  |  |  | 0.1904 |
| 7.56 |  |  |  | 0.1451 |  |
| 7.68 | 0.0786 |  |  |  |  |
| 7.77 |  | 0.0721 |  |  |  |
| 7.81 |  |  | 0.0735 |  |  |
| 8.10 |  |  |  |  | 0.0498 |
| 8.46 |  |  |  | 0.0313 |  |
| 8.50 | 0.0286 |  |  |  |  |
| 8.55 |  |  | 0.0328 |  |  |
| 8.67 |  |  |  |  | 0.0311 |
| 9.93 |  | 0.0234 |  |  |  |
| 9.94 |  |  |  | 0.0250 |  |
| 10.05 |  |  | 0.0241 |  |  |
| 10.09 | 0.0218 |  |  |  |  |
| 10.11 |  |  |  |  | 0.0222 |

FIG. 1 clearly shows that the solubility of brimonidine tartrate increases at a given pH as a function of CMC concentration. For example, at pH 7.5, the sample with 0% CMC resulted in 1000 ppm of Brimonidine tartrate; 0.056% CMC, 1300 ppm; 0.17% CMC, 1300 ppm; and 0.5%, 1600 ppm. At pH 7.5, the sample with 1.5% CMC resulted in about 1400 ppm, which is less than that of a similar solution with CMC at 0.5%. It is unclear at this point what the cause of this observation may be. Nonetheless, brimonidine tartrate is more soluble in solution with a 1.5% CMC than with no CMC.

Nonetheless, brimonidine tartrate is clearly more soluble in solution with a 1.5% CMC than with no CMC.

CMC is also effective to solubilize Brimonidine tartrate in a biological environment, for example the biological environment of the cornea.

Example 3

Brimonidine tartrate is added to a test tube containing a composition including chlorite. The test tube was allowed to equilibrate for ten days. Samples obtained from the test tube are analyzed by HPLC using a size exclusion column in the presence or absence of a chaotrope, such as urea. It is observed that a portion of the brimonidine tartrate monomer units have conjugated to form dimmers, as measured by the apparent molecular weights of brimonidine in solution.

Example 4

Brimonidine tartrate was formulated for ophthalmic topical delivery at pH 7.2 and a concentration of 0.15% (w/v) in an aqueous solution containing PURITE® as a preservative. The ocular hypotensive efficacy of this formulation was determined in human clinical subjects, and compared to the efficacy of ALPHAGAN®, which contains 0.2% brimonidine tartrate, formulated in aqueous ophthalmic topical solution at pH 6.5 in a citrate buffer with 0.05% benzalkonium chloride as a preservative. A third formulation containing 0.2% (w/v) brimonidine tartrate and a PURITE® preservative was also included as a control.

381 human subjects diagnosed with glaucoma or ocular hypertension were randomly assigned to take one of the three formulations at a dosage of one drop into each affected eye three times daily for 12 months. Intraocular pressure (IOP) is measured at two weeks, six weeks, 3 months, 6 months, 9 months and 12 months.

At the end of the 12 month period, the results indicated that there was no significant difference in the hypotensive efficacy of a solution containing 25% less of the active ingredient (0.15% brimonidine) when formulated at pH 7.2, as compared to the ALPHAGAN® product (0.2% brimonidine formulated at pH 6.5). However, those subjects receiving 0.15% brimonidine reported a lower incidence of side effects, such as allergic conjunctivitis, oral dryness, conjunctival hyperemia, and eye discharge, as compared to the higher (0.2%) concentration of brimonidine. These differences are not seen in the 0.2% brimonidine solutions containing PURITE®, and thus are not attributable to the difference in preservatives.

Example 5

A 0.1% brimonidine tartrate solution at pH 7.7 was made as follows:

TABLE V

Brimonidine-Purite 0.1% Ophthalmic Solution.

| Ingredient | Concentration (% w/v) | Concentration (mg/g) |
|---|---|---|
| Brimonidine Tartrate | 0.1 | 1.0 |
| Carboxymethylcellulose Sodium | 0.5 | 5.0 |
| Stabilized Oxychloro Complex (Purite ®) | 0.005 | 0.05 |
| Boric Acid | 0.6 | 6.0 |
| Sodium Borate Decahydrate | 0.045 | 0.45 |
| Sodium Chloride | 0.37 | 3.7 |
| Potassium Chloride | 0.14 | 1.4 |
| Calcium Chloride Dihydrate | 0.006 | 0.06 |
| Magnesium Chloride Hexahydrate | 0.006 | 0.06 |
| Sodium Hydroxide | adjust to pH 7.7 | adjust to pH 7.7 |
| Hydrochloric Acid | adjust to pH 7.7 | adjust to pH 7.7 |
| Purified Water | q.s. to 100% | q.s. to 100% |

Example 6

A topical aqueous ophthalmic solution comprising 0.1% (w/v) brimonidine tartrate formulated at pH 7.7 ("BP 0.1%") as indicated in Example 5, was made for testing in human clinical subjects suffering from high IOP, and the efficacy of this solution compared to the efficacy of ALPHAGAN®, (0.2% brimonidine tartrate formulated in an citrate-buffered aqueous ophthalmic topical solution at pH 6.5 with 0.05% benzalkonium chloride as a preservative).

433 human clinical subjects were randomly chosen to receive one drop of one of the two solutions in the affected eye three times daily. Intraocular pressure is measured at baseline (day 0), three weeks, six weeks, and 3 months.

The results were as follows:
Baseline
  The hour 0 IOP was identical for the two groups (24.7 mm Hg), and the hour 2 (~23 mm Hg) and hour 8 (~22 mm Hg) IOPs were similar for the two groups.
Post-Baseline Hour 0 IOP
  Mean IOP ranges for hour 0 post-baseline readings over the 3-month follow-up period were:
    20.7 to 21.4 mm Hg (BP 0.1%)
    21.0 to 21.7 mm Hg (ALPHAGAN®)
Post-Baseline Diurnal IOP
  Results at post-baseline time points were, in general, similar between the treatment groups. At Month 3, ranges for the diurnal IOP group means at hours 0, 2, and 8 were as follows:
    17.2 to 21.4 mm Hg (BP 0.1%)
    17.6 to 21.7 mm Hg (ALPHAGAN®)
This study shows that, as between the BP 0.1% and the ALPHAGAN® formulations, the subjects experienced substantially equivalent efficacy over the period of the study.

These results were completely unexpected. However, probably because the BP 0.1% only contained 50% the amount of the active ingredient, brimonidine tartrate, as did the ALPHAGAN® formulation, the number of reported incidents of side effects such as oral dryness, asthenia, and eye pruritus were lower in the BP 0.1% group as in the ALPHAGAN® group.

Example 7

Another variation of the formulation of 0.1% brimonidine tartrate at pH 7.7 may be made according to the following table:

| Ingredient | Concentration (% w/v) | Concentration (mg/ml) |
|---|---|---|
| Brimonidine Tartrate | 0.1 | 1.0 |
| Carboxymethylcellulose Sodium | 0.5 | 5.0 |
| Benzalkonium chloride (BAK) | 0.005-0.01 | 0.05-0.1 |
| Sodium Phosphate (septahydrate) | 0.732 | 7.32 |
| Sodium Citrate (Dihydrate) (optional) | 0.1 | 1.0 |
| Sodium Chloride | 0.66-0.69 | 6.6-6.9 |
| Sodium Hydroxide | adjust to pH 7.7 | adjust to pH 7.7 |
| Hydrochloric Acid | adjust to pH 7.7 | adjust to pH 7.7 |
| Purified Water | q.s. to 100% | q.s. to 100% |

Example 8

Another variation of the formulation of 0.1% brimonidine tartrate at pH 7.7 may be made according to the following table:

| Ingredient | Concentration (% w/v) | Concentration (mg/ml) |
|---|---|---|
| Brimonidine Tartrate | 0.1 | 1.0 |
| Polyvinyl alcohol (PVA) | 0.1-1 | 1-10.0 |
| Preservative (e.g., cetrimide, chlorexidine, Polyquad, or PHMB) | 0.001-0.01 | 0.01-0.1 |
| Sodium Phosphate (septahydrate) | 0.732 | 7.32 |
| Sodium Citrate (Dihydrate) (optional) | 0-0.1 | 0-1 |
| Sodium Chloride (optional) | 0-0.69 | 0-6.9 |
| Sodium Hydroxide | Adjust to pH 7.7 | adjust to pH 7.7 |
| Hydrochloric Acid | Adjust to pH 7.7 | adjust to pH 7.7 |
| Purified Water | q.s. to 100% | q.s. to 100% |

It will be understood that sodium salts may be substituted by salts of other metal cations, such as potassium or calcium. If present, tonicity agents may be salts or non-ionic tonicity enhancers, such as glycerin. Buffers may be made with any agent having the appropriate buffering capacity at the chosen pH. The concentrations given above are by way of example, and to not limit the invention in its broader aspects.

While this invention has been described with respect to various specific examples and embodiments, it is to be understood that the invention is not limited thereto and that it can be practiced with considerable variation within the scope of the following claims by those skilled in the art.

What is claimed is:

1. A therapeutically effective aqueous ophthalmic composition for lowering intraocular pressure comprising: a solution containing 0.1% (w/v) of a compound selected from the group consisting of brimonidine, a salt of brimonidine, wherein the solution further comprises an oxy-chloro preservative and carboxymethylcellulose, wherein the composition has a pH between 7.0-8.0.

2. The composition of claim 1 which comprises about 0.1% (w/v) of brimonidine tartrate.

3. The composition of claim 1 which comprises 0.1% (w/v) of brimonidine tartrate.

4. The composition of either of claim 3 wherein the carboxymethyl cellulose enhances the solubility of brimonidine tartrate in solution.

5. The composition of claim 3 wherein the oxy-chloro component is Purite.

6. The composition of claim 3 further comprising boric acid.

7. The composition of claim 3 further comprising sodium borate.

8. The composition of claim 3 further comprising hydrochloric acid.

9. The composition of claim 8 wherein the composition has a pH of 7.4-8.0.

* * * * *

UNITED STATES PATENT AND TRADEMARK OFFICE
CERTIFICATE OF CORRECTION

PATENT NO.         : 8,858,961 B2
APPLICATION NO.    : 12/482783
DATED              : October 14, 2014
INVENTOR(S)        : Richard S. Graham et al.

It is certified that error appears in the above-identified patent and that said Letters Patent is hereby corrected as shown below:

In the Specification,

In column 7, line 53, delete "SECS." and insert -- SECs. --, therefor.

In column 14, line 38, delete "chlorbutol" and insert -- chlorobutol --, therefor.

In the Claims,

In column 23, line 17, in claim 5, delete "Purite." and insert -- chlorine dioxide. --, therefor.

Signed and Sealed this
Third Day of February, 2015

Michelle K. Lee
*Deputy Director of the United States Patent and Trademark Office*